US012569609B2

(12) United States Patent
Koenig et al.

(10) Patent No.: US 12,569,609 B2
(45) Date of Patent: Mar. 10, 2026

(54) TEMPERATURE MANAGEMENT SYSTEM FOR PATIENTS DURING STATIONARY AND MOBILE ECLS/ECMO THERAPY

(71) Applicant: IRASUN GMBH, Munich (DE)

(72) Inventors: Fabian Koenig, Unterfoehring (DE); Florian Altinger, Munich (DE)

(73) Assignee: IRASUN GMBH, Munich (DE)

( * ) Notice: Subject to any disclaimer, the term of this patent is extended or adjusted under 35 U.S.C. 154(b) by 204 days.

(21) Appl. No.: 16/953,300

(22) Filed: Nov. 19, 2020

(65) Prior Publication Data

US 2022/0062521 A1      Mar. 3, 2022

(30) Foreign Application Priority Data

Nov. 19, 2019    (EP) ..................................... 19000524

(51) Int. Cl.
A61M 1/36          (2006.01)
A61M 1/16          (2006.01)
(52) U.S. Cl.
CPC .......... A61M 1/369 (2013.01); A61M 1/1698 (2013.01); A61M 1/3607 (2014.02); A61M 1/3623 (2022.05); A61M 2205/15 (2013.01); A61M 2205/36 (2013.01)
(58) Field of Classification Search
CPC .............. A61M 1/1698; A61M 1/3607; A61M 1/3623; A61M 1/369; A61M 60/109; A61M 60/232; A61M 60/38; A61M 2205/15; A61M 2205/273; A61M 2205/3576; A61M 2205/36; A61M 2205/366
See application file for complete search history.

(56) References Cited

U.S. PATENT DOCUMENTS

| | | | | |
|---|---|---|---|---|
| 5,489,413 | A | * | 2/1996 | Carson .................. F28F 21/062 |
| | | | | 422/46 |
| 5,770,149 | A | * | 6/1998 | Raible ................. A61M 60/806 |
| | | | | 422/46 |
| 9,351,869 | B2 | | 5/2016 | Knott et al. |
| 9,867,921 | B2 | | 1/2018 | Hedmann et al. |
| 9,987,412 | B2 | | 6/2018 | Ahrens et al. |
| 10,022,507 | B2 | | 7/2018 | Cassidy |
| 10,473,365 | B2 | | 11/2019 | Bell et al. |
| 10,605,497 | B2 | | 3/2020 | Rappl et al. |
| 11,026,833 | B2 | | 6/2021 | Knott et al. |

(Continued)

FOREIGN PATENT DOCUMENTS

| | | | |
|---|---|---|---|
| DE | 102017217782 | A1 | 4/2019 |
| EP | 1371381 | A1 | 12/2003 |

(Continued)

*Primary Examiner* — Patrick Orme
(74) *Attorney, Agent, or Firm* — McCoy Russell LLP

(57)          ABSTRACT

The present invention relates to a system (5) for temperature management for patients in stationary and mobile ECLS and/or ECMO therapy, with at least one disposable (7) and a fluid circuit (9), wherein the disposable (7) comprises at least one reservoir (10) or bag provided with at least one supply line (12) and a drain line (14), further provided at least one pumping unit element (11) as part of the disposable (7), by means of which liquid in the reservoir (10) or bag can be pumped through the fluid circuit (9).

Furthermore, the present invention relates to a disposable (7) for such a system (5).

19 Claims, 3 Drawing Sheets

(56)                    References Cited

U.S. PATENT DOCUMENTS

| | | | |
|---|---|---|---|
| 2003/0126910 A1* | 7/2003 | Burbank | A61M 1/367 |
| | | | 73/40 |
| 2007/0253463 A1* | 11/2007 | Perry | G05D 7/0682 |
| | | | 374/208 |
| 2017/0173262 A1* | 6/2017 | Veltz | G16H 20/17 |
| 2019/0160216 A1 | 5/2019 | Pouchoulin | |
| 2019/0209762 A1* | 7/2019 | Turner | A61M 1/3666 |
| 2019/0316948 A1* | 10/2019 | Karol | A61M 1/1565 |
| 2019/0326498 A1 | 10/2019 | Spillner | |
| 2019/0351422 A1 | 11/2019 | Demou et al. | |
| 2020/0130457 A1 | 4/2020 | Bell et al. | |
| 2020/0261636 A1 | 8/2020 | Kechele | |
| 2020/0276376 A1 | 9/2020 | Wolfgramm et al. | |
| 2020/0282126 A1 | 9/2020 | Pouchoulin | |
| 2020/0284471 A1 | 9/2020 | Newell | |
| 2020/0289316 A1 | 9/2020 | Eller | |
| 2021/0060230 A1 | 3/2021 | Hopper et al. | |
| 2021/0100944 A1 | 4/2021 | Wangen | |
| 2022/0249751 A1 | 8/2022 | Kammerzell et al. | |

FOREIGN PATENT DOCUMENTS

| | | | |
|---|---|---|---|
| WO | 2017148984 A1 | 9/2017 | |
| WO | 2018099593 A1 | 6/2018 | |
| WO | 2018140414 A1 | 8/2018 | |
| WO | 2020074357 A1 | 4/2020 | |
| WO | 2020081991 A2 | 4/2020 | |
| WO | 2020081995 A2 | 4/2020 | |
| WO | 2020112902 A1 | 6/2020 | |
| WO | 2021137116 A1 | 7/2021 | |

* cited by examiner

TEMPERATURE MANAGEMENT SYSTEM FOR PATIENTS DURING STATIONARY AND MOBILE ECLS/ECMO THERAPY

CROSS-REFERENCE TO RELATED APPLICATION

The present application claims priority to European Patent Application No. 19000524.9, entitled "TEMPERATURE MANAGEMENT SYSTEM FOR PATIENTS DURING STATIONARY AND MOBILE ECLS/ECMO THERAPY", and filed on Nov. 19, 2019. The entire contents of the above-listed application is hereby incorporated by reference for all purposes.

TECHNICAL FIELD

This invention relates to a system for patient blood temperature management, applied for example to patients during stationary and mobile ECLS/ECMO therapy, an assembly comprising a system and a medical device and a method for operating a system for patient temperature management.

BACKGROUND

Circulatory diseases (which include heart disease and stroke) have remained the most common cause of death in the Western world. In Europe, more than 275,000 people per year suffer cardiac arrest outside of clinical settings. Even with immediate onset of conventional cardiopulmonary resuscitation (CPR), survival with no or minimal neurological damage is minimal. An alternative to conventional CPR is extracorporeal membrane oxygenation (ECMO). In addition, comprehensive treatment of patients is usually only possible in specialized centers. However, the stabilization of patients for transport is very difficult in most cases. Here as well, ECMO offers new alternatives.

Extracorporeal membrane oxygenation (ECMO) is a machine-based cardiovascular support that can support or completely replace both the pulmonary oxygenation of the blood as well as the pumping function of the heart. It represents a promising but also highly invasive therapy option, which was initially used purely as "ultima ratio" therapy. Low experience combined with a high-risk patient clientele resulted in high mortality rates. With increasing experience and improved medical devices and therapies, initial problems have been resolved and complication rates significantly reduced. Contraindications to the use of ECMO therapy—also known as Extra Corporeal Life Support (ECLS)—have been greatly reduced. ECMO therapy quickly spread to new fields of application and indications, and new therapeutic approaches were developed. In addition to resuscitation during cardiac arrest and treatment of respiratory failure, the ECMO therapy also provides a bridging solution (bridge to transplant, bridge to VAD (ventricular assist device)). Another important application is the ability to treat patients with cardiogenic shock or under resuscitation for transport to a specialized center to stabilize. In pediatrics, ECMO now also plays a central role, especially as it is often the only therapy option besides a VAD.

ECMO therapy is now an established intensive care therapy and is one of the standard procedures at cardiac surgery centers. The survival rate improved to an average of 68% in 2017, which is a great success given the high-risk clientele. The average survival of all ECMO patients from 1986 to 2006 was approximately 50%.

ECMO systems are known for example from U.S. Pat. No. 5,770,149A.

A central component of said systems are oxygenators. Oxygenators enrich the patient's blood with oxygen. By monitoring the blood flow and controlling the gas blender, it is always possible to ensure the optimal oxygen or carbon dioxide content in the blood.

Since the patient's blood is passed through long external tubes, it cools down significantly. The energy loss is so high that the body cannot compensate for it independently. In order to avoid lowering the body core temperature, it is necessary to induce heat energy into the patient. For this purpose, the oxygenators of the ECLS systems offer an integrated heat exchanger. In addition, if necessary, e.g. to reduce the oxygen consumption in the organism, the heat exchangers in the oxygenator are used to cool the patient.

Heat exchange oxygenators are known, for example, from EP1371381A1.

Controlling the patient blood temperature indirectly by use of a water cycle through the oxygenators heat exchanger is also utilized during the use of the heart-lung machine. Thus, devices already exist for this application. However, as these have to offer the option of cooling the patients in addition to the heating function, they are referred to as hypothermia devices. These have an open water tank and are with an overall weight of more than 100 kg not suitable for mobile use. Their intended use is purely in the temperature control of patients during cardio-surgical operations utilizing heart-lung machines.

Hypothermia devices are known for example from DE102017217782A1.

Current hypothermia devices on the market have the considerable and central disadvantage that they work with a water reservoir and fixed stationary pumps and tubes. A complete and clinically correct cleaning of the system is therefore extremely complex and highly difficult to carry out. Improperly performed cleaning of the system can lead to contamination in the immediate area. Because these systems are typically placed in the intensive care unit as close to the patient as possible, the risk to contaminate the patient must be considered.

While several compact, portable ECLS systems have been developed, a specialized temperature management device for that dedicated purpose and application has not yet been developed. Currently used temperature control devices connected to the heat exchanger of the oxygenator were originally developed to control the temperature of heating mats. In terms of safety, hygiene and practicability, these devices have significant shortcomings when combined with ECLS systems.

Another disadvantage of previous systems is that due to their architecture and method of action, they are only approved for stationary use. With increasing applications during transport and out of hospital, a mobile solution for temperature management is required. Ideally, all types of patient transportation should be considered, including transportation in rescue helicopters, aircrafts and ambulances. There is currently no approved device available on the market.

Therefore, there exists an acute clinical need for a system which overcomes these disadvantages. The object of this invention is to provide a temperature management system for ECMO/ECLS systems, which is developed and optimized for this specific application. First and foremost, the risk of contamination is eliminated due to its design and mode of operation.

SUMMARY

This object is achieved by a system for temperature management for patients during stationary and mobile ECLS and/or ECMO operation with the features of claim 1. Accordingly, a system for temperature management for patients in stationary and mobile ECLS and/or ECMO therapy is provided, with at least one disposable and a fluid circuit, wherein the disposable comprises at least one reservoir or bag provided with at least one supply line and a drain line, further provided at least one pumping unit element as part of the disposable, by means of which liquid in the reservoir or bag can be pumped through the fluid circuit.

The pumping function can also be performed by at least one roller pump. The circulation transports the heating fluid from the reservoir/bag—which is placed in a heating unit outside of the disposable—into the oxygenator and back. The fluid temperature in the reservoir/bag can be precisely regulated by means of regulation on the heating unit, and consequently the blood temperature of the patient can be regulated, while the risk of contamination of the patient can be avoided.

The circuit can comprise the usual components of an ECLS and/or ECMO circuit, such as a heating unit and/or an oxygenator and/or one or more heat exchanger and/or blood lines (venous line(s) and arterial line(s)) etc.

The system and the disposable are designed and set up in a way, that by regulating the heating unit, the liquid temperature in the reservoir or bag can be precisely regulated, and consequently the blood temperature of the patient can be controlled while the risk of contamination can be eliminated.

The invention is based on the idea that the risk of contamination should be eliminated by design. All components in contact with the fluid are disposed of after a single use. This includes, for example, a liquid bag, which serves as a reservoir, the centrifugal pump head and the associated hoses. The complete disposable is designed as a sterile set. The permanent part of the device—which includes but is not limited to—a heating unit, a pump drive, an input device and necessary sensors, is not in contact with the heat-conducting fluid and thus remains free from contamination. Moreover, it is designed in a way to be easily cleaned and disinfected.

Thus, the possibility to control the patient blood temperature is provided. In contrast to available systems, the circulating fluid as well as all connected components are sterile and can be disposed of after the therapy. This way, contamination of the device, the oxygenator or the patient can be impeded.

The disposable can be configured such that it comprises all components which are in direct contact with the heat transfer fluid.

Further, the pumping unit of the system can consist at least of the pumping unit element and a drive, wherein one pumping unit element is a centrifugal pump head being part of the disposable product and further, wherein the drive, which controls the pump head, is a part of the system and not part of the disposable. Thus, in other words, it is possible that the pump unit consists of two parts: The centrifugal pump head which is in contact with the heat exchange fluid is part of the disposable product. The drive which is controlling the pump head is part of the permanent device. It can also be the case that the pump is an external roller pump. In that case, a pump component integrated into the disposable may not be necessary.

Additionally, it is possible that the system comprises at least one heating unit. This may for example be designed such that both sides of the bag/reservoir are heated by means of (a) heating element(s) in order to heat the fluid contained therein to the set target temperature. The heating unit may be not in contact with the heat transfer fluid and is thus part of the permanent system part.

It is possible in a further embodiment of the invention that the system has a validation element configured for validating and invalidating a disposable. Thus, a multiple use and thus a contamination of the set can be eliminated. This can be implemented, for example, via an RFID tag integrated in the hose set, which can be devalued after first use. In other words, it is possible that the system has a function for validating the disposable set.

Furthermore, it can be provided that by means of a Poka-Yoke concept incorrect insertion of the disposable product is prevented by design. A faulty operation by incorrect use is thus not possible.

Furthermore, it can be provided that the system has an automated filling and/or venting function. In particular, in this case and embodiment the system comprises a controller which is configured for an automated filling and/or venting function. For this purpose, it should be designed in a way in which the removal of air bubbles from the system at regular intervals is performed automatically.

It is possible that the system comprises an operating parameter recording module, wherein this module comprises a patient data management interface by means of which data is exchangeable with a patient data management system.

Further, the system can have a synchronization interface, by means of which data is interchangeable with one or more medical devices, in particular wherein via the synchronization interface at least one command for activation or deactivation of the temperature regulating module are interchangeable.

For this purpose, it should be designed in a way in which the removal of air bubbles from the system at regular intervals can be performed automatically.

Additionally, it is possible that the system comprises a leak detector which is configured such that leaks in the hose system are detected automatically. So, it is possible that leaks in the hose system are automatically detected. For example, one or more Sensors forming a leak detector can continuously measure the level in the reservoir bag and inform the user if the level is too low via status messages and warning signals.

Further, the system may comprise a pressure build up avoidance element, which his configured such that a pressure build up in the oxygenator is impossible. The pressure build can be a negative pressure build up or positive pressure build up. So, it is possible that the system is designed in a way to avoid pressure buildup in the disposable and the oxygenator. For this purpose, centrifugal pump heads may be used, which cannot exceed the maximum permissible pressure of the disposable and the oxygenator. In case of the use of roller pumps, this may be achieved by integration of pressure relieve valves into the disposable.

It may also be provided that the system has an inputs and outputs (such as a user interface) by means of which the user is able to input operating parameters, in particular desired values and/or target values and/or product limits and/or maximum limits, and by means of which operating parameters can be output, in particular displayed. The system may this have a graphical user interface, via which target values, warning limits and maximum limits can be defined by the user. By a simple and intuitive input possibility a guided user can input can be made possible and operating errors can be prevented. Errors may lead to acoustic warning messages as well as to visual warning messages, which can be output via the graphical user interface. It is also conceivable that the error causes can also be described on the user interface. It is also conceivable that illustrations for troubleshooting can be displayed or concrete instructions for the next steps in the treatment process can be provided.

Furthermore, the system may be provided with an operating parameter recording module by means of which operating parameters of the system can be monitored and/or recorded. Using such a system, application data such as date, runtime, target value, actual value, warning limits, maximum limits or other operating parameters can be archived in the system in an internal memory. This is also conceivable that the operating parameter recording module is connected to an external storage system in order to archive application data there. For example, in the event of a dispute, the actual pressure processes in the system can be documented and user errors can be ruled out. In addition, such a system can be used for quality assurance.

It is also conceivable that the operating parameter recording module has a patient data management interface by means of which data can be exchanged with a patient data management system. Such a facility will make it possible to simplify data recording and data management associated with the system for patient treatment.

In addition, it may be provided that the system has a synchronization interface by means of which data can be exchanged with one or more medical devices, in particular wherein at least one stop command for activating or deactivating the temperature management system can be exchanged via the synchronization interface. It is conceivable, for example, that a serial interface or other interface with a data input is provided for this purpose. By means of the interface and the corresponding signals transmitted and exchanged via it, other medical devices can turn on or switch off the temperature management system by sending a respective command. This allows the automated synchronization of processes that previously had to be performed manually. The automation of the synchronization in particular increases the user-friendliness and the safety of the patient.

Furthermore, the present invention relates to a method for operating a system for temperature management, the method having at least the following steps:

the fluid circuit is permanently monitored with multiple sensors, based on these sensor values, the actual fluid temperature is calculated, the heating unit is regulated based on the delta between the current temperature value and the target temperature value Additionally, the present invention relates to a disposable for a system as described above. Such a disposable comprises the features of the disposable as described in this disclosure. Further, the disposable is configured and arranged to be used with the system and its preferred embodiment as described in the present disclosure.

BRIEF DESCRIPTION OF THE FIGURES

Further details and advantages of the invention will now be explained with reference to an embodiment shown in more detail in the drawings. The described embodiments are to be considered in all respects only as illustrative and not restrictive, and various combinations of the recited features are included in the invention.

It shown in.

DETAILED DESCRIPTION

Figure 1:
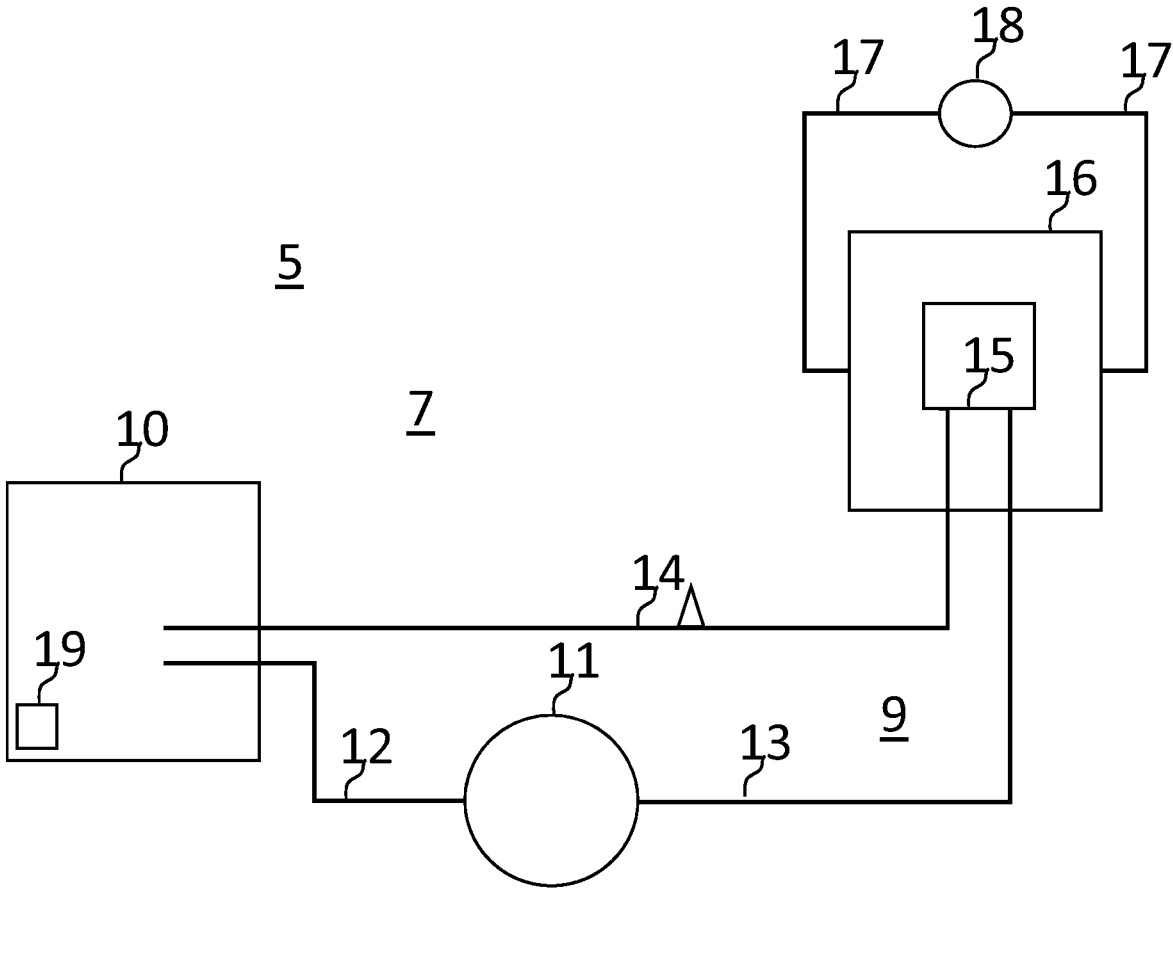
FIG. 1 a schematic overview of an embodiment of the disposable product in combination with the oxygenator.

FIG. 1 shows a schematic representation of the system 5 according to an embodiment of the present invention with the assembled disposable 7 consisting of several single components, as well as the connection to the existing system 5 with a fluid circuit 9, having an oxygenator and also showing the blood circulation of the patient.

The disposable comprises a bag/reservoir 10, which is connected via a hose 12 to the centrifugal pump head 11. Furthermore, a hose 13 is contained starting from the pump head for connection to the oxygenator 16—in particular to the inlet of the heat exchanger 15 of the oxygenator 16.

Another tube 14 leads from the outlet of the heat exchanger 15 of the oxygenator 16 back to the bag 10 and thus closes the circuit. In addition, a three-way spigot may be integrated in the hose 14. This can be used for initial filling and/or for venting the system.

Furthermore, in FIG. 1, the typical prior art structure of the blood circulation through the oxygenator is shown schematically. The blood of the patient is guided with tubes 17 through the oxygenator and thereby oxygenated. Also included in the circuit are typically a pump, a blood reservoir, and the patient 18.

Also contained in the disposable is a device 19 for storing relevant data (e.g., production date, expiration date, serial number, etc.). In addition, the disposable may be invalidated after first use. Multiple use of a disposable set can thus be eliminated. For example, an RFID tag can be used for this purpose.

Figure 2:
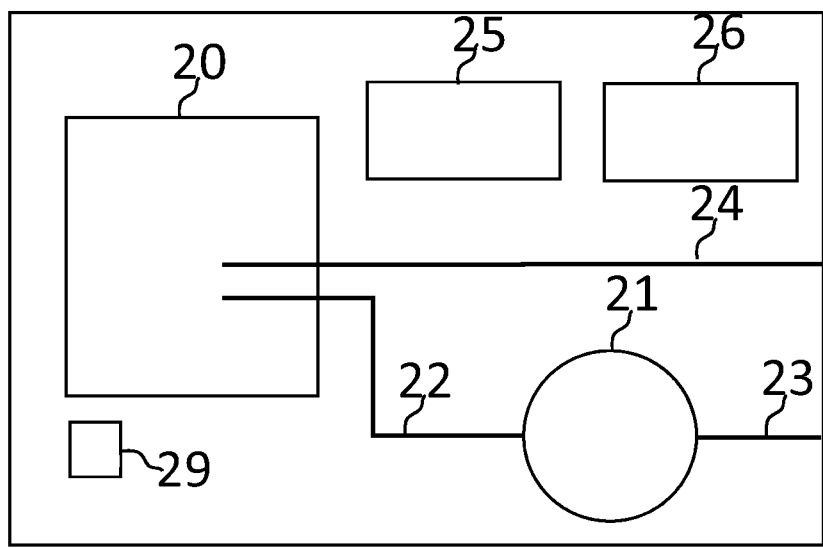
FIG. 2 a schematic overview of an embodiment of the permanent device, in which the disposable used in FIG. 1 can be inserted and operated.

FIG. 2 schematically shows the structure of the permanent device, in which the disposable product can be inserted and used.

The heating unit 20 can be designed, for example, as a double-sided metal surface with an attached heating foil, which heats the bag to the desired temperature with heat conducting means located therein on both sides. The heating unit 20 is not in direct contact with the heat conduction.

Via a hose guide 22, the safe and error-free use of the disposable product can be ensured. Here, the Poka-Yoke principle can be used. The pump head can be used in the specially manufactured pump head holder with the drive of the pump 21, for example by means of bayonet closure and secured against unintentional loosening. Via the hose guide 23, the hose 13 can be guided to the oxygenator.

Via the hose guide 24, the hose of the return is fixed in the bag 10 and secured. An incorrect insertion of the hose or an unwanted kinking can be avoided.

To avoid the multiple use of a disposable set, a sensor 29, such as an NFC sensor, is integrated with the permanent device which checks the RFID tag 19 in the disposable 7 for correctness (e.g., expiration date or prior use) and may invalidate it. Possible contamination through reuse can be made impossible.

Furthermore, all control functions and control algorithms can be integrated into a control unit 26, for example a board with integrated electronics and algorithms. This may include the control of the display, the pump and/or the heating unit, as well as the evaluation of sensors such as the NFC sensor and various temperature sensors which may be integrated in the heating unit.

In addition, the control unit 26 may comprise of an operating parameter recording module, by means of which operating parameters of the system can be monitored and/or recorded.

The control unit 26 may further comprise a patient data management interface by means of which data is exchangeable with a patient data management system. For this purpose, the system may have a corresponding interface, which is formed here by a common synchronization interface. It is also conceivable that the patient data management interface communicates with other medical devices via wireless technologies.

Incidentally, it is conceivable that the control unit 26 may be formed by means of a synchronization interface. For example, a stop signal or a start command can be received by other medical devices connected to the overall system via the synchronization interface. Further, for example, a stop signal or warning signal may be sent to and/or forwarded to other medical devices in communication with the system. In addition, data can be exchanged via the synchronization interface.

Figure 3:
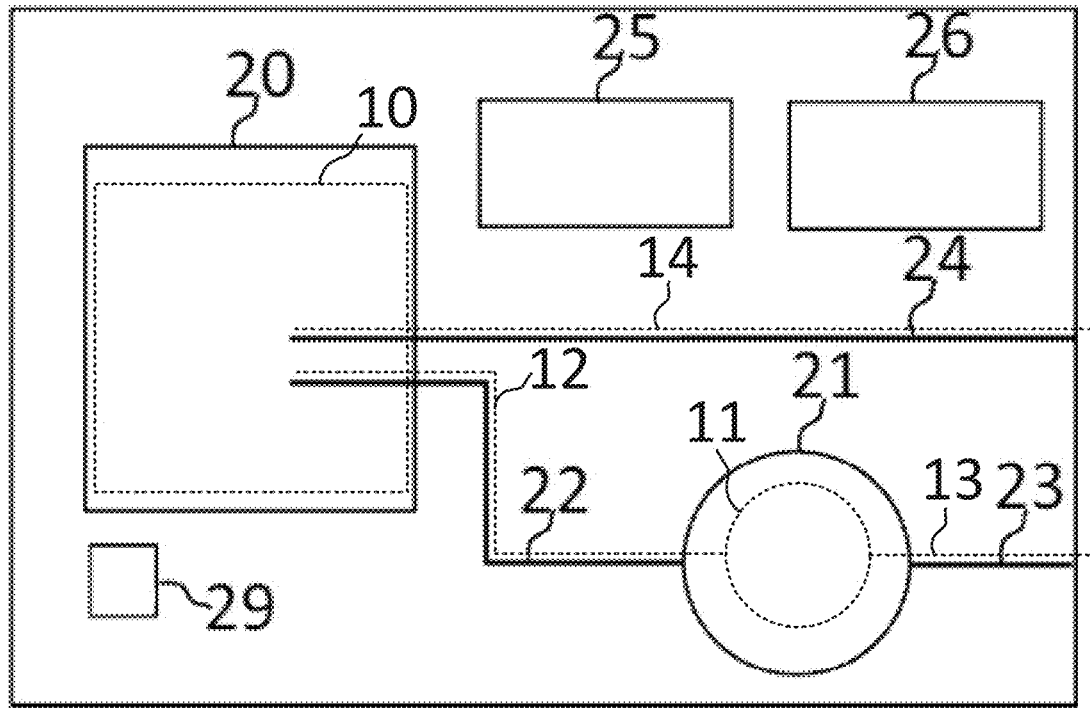
FIG. 3 a schematic overview of an embodiment of the disposable product inserted into the permanent device.

By way of example, the following routine is conceivable for inserting the disposable set from FIG. 1 into the permanent device from FIG. 2 to create the configuration shown in FIG. 3:

1. Inserting the bag 10 in the fixture of the heating unit 20.
2. Guide the tube 12 along the predetermined tube guide 22.
3. Inserting centrifugal pump head 11 in the pump head fixture 21 and engage by using bayonet mechanism.
4. Guide the hose 13 along the predetermined hose guide 23.
5. Connecting the hose 13 to the inlet of the heat exchanger 15 of the oxygenator 16.
6. Connecting the hose 14 at the outlet of the heat exchanger 15 of the oxygenator 16.
7. Guide the hose 14 along the predetermined hose guide 24.
8. Fill the disposable set with sterile fluid (e.g. NaCl) or unsterile fluid (e.g. water) by using the three-way spigot on hose 14.
9. If necessary, use three-way spigot on hose 14 to vent air.

REFERENCE NUMBERS

5 System
7 Disposable
9 Fluid Circuit
10 Bag/reservoir
11 Centrifugal pump head
12 Hose to centrifugal pump head
13 Tube to oxygenator
14 Tube from oxygenator with three-way spigot
15 Heat exchanger of the oxygenator
16 Oxygenator
17 Blood-bearing tubes
18 Pump, blood reservoir and patient
19 Device for storing relevant data
20 Heating unit
21 Pump drive
22 Hose guide to centrifugal pump head
23 Hose guide to oxygenator
24 Hose guide from the oxygenator with three-way spigot

25 Display
26 Control unit
29 Sensor for reading the data in the disposable set

The invention claimed is:

1. A system for temperature management for a patient in stationary and mobile extracorporeal life support (ECLS) and/or extracorporeal membrane oxygenation (ECMO) therapy, the system comprising:
  a disposable, comprising:
    at least one bag configured to hold a heat transfer fluid;
    a heat transfer fluid circuit having a supply line and a drain line; and
    at least one pumping unit element configured to pump the heat transfer fluid in the at least one bag through the heat transfer fluid circuit, the at least one pumping unit element being part of the disposable;
  a blood circuit configured to transport blood through a patient, the blood circuit including at least one blood tube, a blood pump, a blood reservoir, and an oxygenator having a heat exchanger configured to receive the heat transfer fluid from the at least one pumping unit element through a first hose, the oxygenator being configured to oxygenate blood of the patient; and
  a permanent device configured to receive the disposable, the permanent device having at least one heating unit, the at least one bag configured to be housed in the at least one heating unit, wherein the at least one heating unit is configured to heat the heat transfer fluid held within the at least one bag,
  wherein the supply line includes a tube between the at least one bag and the at least one pumping unit element, and further wherein the drain line includes a second hose between the heat exchanger and the at least one bag.

2. The system according to claim 1, wherein the disposable is configured such that the disposable comprises all components which are in direct contact with the heat transfer fluid, wherein the at least one pumping unit element comprises a centrifugal pump head, and wherein the at least one bag, fluid transfer circuit, centrifugal pump head, and heat exchanger form a closed circuit when the fluid transfer circuit is coupled to the heat exchanger, such that the heat transfer fluid is maintained sterile.

3. The system according to claim 1, wherein a pumping unit of the system consists of at least one of the at least one pumping unit element and at least one drive, wherein the at least one pumping unit element is a centrifugal pump head being part of the disposable, and wherein the at least one drive, which controls the centrifugal pump head, is a part of the system and not part of the disposable.

4. The system according to claim 1, wherein the system comprises a controller which is configured for an automated filling and/or venting function.

5. The system according to claim 1, wherein the system comprises an operating parameter recording module, which comprises a patient data management interface by which data is exchangeable with a patient data management system.

6. The system according to claim 1, wherein the system has a synchronization interface, by which data is interchangeable with one or more medical devices, in particular wherein via the synchronization interface at least one command for activation or de-activation of a temperature regulating module of the at least one heating unit are interchangeable.

7. The system according to claim 1, wherein the system comprises a leak detector which is configured such that leaks in the fluid circuit are detected automatically.

8. The system according to claim 1, wherein the system comprises at least one pressure relief valve, which is configured such that a pressure build up in the oxygenator is impossible.

9. The system according to claim 1, wherein the at least one heating unit is a double-sided metal surface with an attached heating foil.

10. The system according to claim 1, wherein the at least one heating unit is configured to heat the at least one bag to a desired temperature with heat conduction located therein on two sides of the at least one bag.

11. The system according to claim 10, wherein the at least one heating unit is not in direct contact with the heat conduction.

12. The system according to claim 1, further comprising a near field communication (NFC) sensor configured to check a radio frequency identification (RFID) tag in the disposable to check for an expiration date of the disposable.

13. The system according to claim 1, wherein the heat transfer fluid is a sterile fluid.

14. The system according to claim 1, the permanent device further having a tube guide to securely receive and guide the tube when the disposable is positioned within the permanent device.

15. The system according to claim 1, the permanent device further having a first hose guide to securely receive and guide the first hose when the disposable is positioned within the permanent device.

16. The system according to claim 1, the permanent device further having a second hose guide to securely receive and guide the second hose when the disposable is positioned within the permanent device.

17. The system according to claim 1, the permanent device further having a pump head holder configured to receive the at least one pumping unit element when the disposable is positioned within the permanent device.

18. The system according to claim 17, wherein the pump head holder is configured to secure the at least one pumping unit element by using a bayonet mechanism.

19. The system according to claim 5, wherein the operating parameter recording module is configured to monitor and/or record at least one operating parameter of the system, and wherein the at least one operating parameter of the system includes at least one of the following: date, runtime, warning limits, and maximum limits.

* * * * *